United States Patent
Green et al.

(10) Patent No.: US 10,371,665 B2
(45) Date of Patent: Aug. 6, 2019

(54) MOBILITY SELECTIVE ATTENUATION

(71) Applicant: Micromass UK Limited, Wilmslow (GB)

(72) Inventors: Martin Raymond Green, Bowdon (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/315,148

(22) PCT Filed: Jun. 5, 2015

(86) PCT No.: PCT/GB2015/051650
§ 371 (c)(1),
(2) Date: Nov. 30, 2016

(87) PCT Pub. No.: WO2015/185941
PCT Pub. Date: Dec. 10, 2015

(65) Prior Publication Data
US 2017/0212081 A1    Jul. 27, 2017

(30) Foreign Application Priority Data

Jun. 6, 2014    (EP) .................................. 14171487
Jun. 6, 2014    (GB) .................................. 1410052.3

(51) Int. Cl.
*G01N 27/62*    (2006.01)
*H01J 49/00*    (2006.01)

(52) U.S. Cl.
CPC .......... *G01N 27/622* (2013.01); *G01N 27/62* (2013.01); *H01J 49/004* (2013.01); *H01J 49/0031* (2013.01)

(58) Field of Classification Search
None
See application file for complete search history.

(56) References Cited

U.S. PATENT DOCUMENTS 6,498,342 B1    12/2002    Clemmer
7,105,808 B2     9/2006    Bromberg et al.
(Continued)

FOREIGN PATENT DOCUMENTS

GB    2413433         10/2005
GB    2413433 A  *  10/2005  ........... G01N 27/624
(Continued)

OTHER PUBLICATIONS

Guevremont, R et al., "*Atmospheric Pressure Ion Trapping in a Tandem FAIMS-FAIMS Coupled to a TOFMS: Studies with Electrospray Generated Gramicidin S Ions*", Journal of the American Society for Mass Spectrometry, vol. 12, No. 12, pp. 1320-1330, (Dec. 2001).

*Primary Examiner* — Andrew Smyth
(74) *Attorney, Agent, or Firm* — Womble Bond Dickinson (US) LLP; Deborah M. Vernon; Heath T. Misley (57) ABSTRACT

A method of mass spectrometry is disclosed comprising separating a first population of ions according to their ion mobility and selectively attenuating ions in the first population of ions in one or more ion mobility and/or drift time ranges so as to form a second population of ions. The step of selectively attenuating ions comprises applying a varying, increasing or decreasing attenuation factor to ions in different ion mobility and/or drift time ranges. The method further comprises separating the second population of ions according to their ion mobility.

19 Claims, 2 Drawing Sheets

(56) References Cited

U.S. PATENT DOCUMENTS

| | | |
|---|---|---|
| 7,683,314 B2 | 3/2010 | Green et al. |
| 8,445,845 B2 | 5/2013 | Green et al. |
| 9,520,279 B2 | 12/2016 | Batman et al. |
| 2002/0014586 A1 | 2/2002 | Clemmer |
| 2003/0001084 A1* | 1/2003 | Bateman ............... H01J 49/004 250/281 |
| 2003/0132379 A1* | 7/2003 | Li ........................ G01N 27/622 250/286 |
| 2005/0189486 A1* | 9/2005 | Fuhrer .................. G01N 27/622 250/287 |
| 2006/0027746 A1* | 2/2006 | Guevremont ........ G01N 27/624 250/292 |
| 2006/0219889 A1* | 10/2006 | Shvartsburg ......... G01N 27/624 250/282 |
| 2007/0278397 A1* | 12/2007 | Bateman ............... G01N 27/622 250/286 |
| 2008/0135746 A1* | 6/2008 | Wildgoose ............ H01J 49/005 250/283 |
| 2010/0065733 A1* | 3/2010 | Bateman ............... H01J 49/004 250/282 |
| 2011/0068264 A1* | 3/2011 | Xu ........................ G01N 27/622 250/286 |
| 2011/0095175 A1* | 4/2011 | Bateman ............... G01N 27/624 250/282 |
| 2011/0183431 A1* | 7/2011 | Covey .................. G01N 27/624 436/173 |

FOREIGN PATENT DOCUMENTS

| | | | | |
|---|---|---|---|---|
| GB | 2413433 A | * | 10/2006 | |
| GB | 2413433 B | * | 10/2006 | |
| GB | 2413433 B | * | 3/2007 | .......... G01N 27/624 |
| GB | 2502650 | | 12/2013 | |
| GB | 2502650 A | * | 12/2013 | .......... H01J 49/0031 |
| GB | 2502650 A | * | 12/2013 | |
| GB | 2502650 B | * | 12/2013 | |
| GB | 2502650 B | * | 6/2016 | .......... H01J 49/0031 |

* cited by examiner

MOBILITY SELECTIVE ATTENUATION

CROSS-REFERENCE TO RELATED APPLICATIONS

This application represents the U.S. National Phase of International Application No. PCT/GB2015/051650 entitled "Mobility Selective Attenuation" filed 5 Jun. 2015, which claims priority from and the benefit of United Kingdom patent application No. 1410052.3 filed on 6 Jun. 2014 and European patent application No. 14171487.3 filed on 6 Jun. 2014. The entire contents of these applications are incorporated herein by reference.

FIELD OF THE INVENTION

The present invention relates generally to mass spectrometry and in particular to mass spectrometers and methods of mass spectrometry. Various embodiments relate to apparatus and methods of reducing space charge and saturation effects in ion mobility spectrometry experiments.

BACKGROUND

In many cases the population of ions transmitted to an ion mobility spectrometer or separator contains ion species which are either not of interest to a particular analysis or are in such high abundance that they can cause either saturation of a downstream ion detector or distort the drift time or peak shape recorded in ion mobility separations due to space charge interaction.

The presence of such ion species within an analytical ion mobility spectrometer or separator ("IMS") device can lead to non-optimum performance of the ion mobility spectrometer or separator.

Distortions due to space charge interaction can occur for high charge densities within specific ion mobility ranges since ions within these regions may experience high charge density for most or all of their transit time through the ion mobility spectrometer or separator.

U.S. Pat. No. 7,105,808 (Bromberg) discloses an arrangement comprising an atmospheric pressure drift tube with an ion shutter grid and an upstream pre-concentrator. The pre-concentrator consists of a series of at least two grids. Ions of high mobility are selectively removed as they travel further into the pre-concentrator region and are neutralised on the surface of a grid. Ions pass through several grids resulting in more transmission losses.

Ions are gated into the pre-concentrator region for a very short period of time (e.g. about 100-200 ms) and are then oscillated back and forth between two grids to allow depletion of the high mobility species. The remaining ions are then gated into the ion mobility drift tube and separated. Most of the ions created in the ion source are lost as no ions are accumulated prior to the pre-concentrator.

The small portion of the ion population gated into the pre-concentrator region may not be allowed to reside for an indefinite period as radial diffusion of the ion cloud will either exceed the radius of the drift tube during pre-concentration or subsequently during ion mobility separation and hence ions will be lost to the walls of the drift tube.

It should be noted that pre-concentration in this case refers to the enriching of the ion population with respect to low mobility ions.

According to the arrangement disclosed in U.S. Pat. No. 7,105,808 (Bromberg) all ions above a certain mobility are lost to the system before the remaining ions are transferred to the ion mobility drift tube. It is not therefore possible to control the amount of high mobility ions that are transferred.

Furthermore, the system disclosed in U.S. Pat. No. 7,105,808 (Bromberg) suffers from a low duty cycle since the arrangement of the grids and pre-concentrator causes numerous transmission losses.

Attenuation devices are known. Reference is made, for example, to the arrangements disclosed in U.S. Pat. No. 7,683,314 (Micromass).

US 2002/0014586 (Clemmer) discloses an instrument for separating ions in time as functions of preselected ion mobility and ion mass.

U.S. Pat. No. 6,498,342 (Clemmer) discloses an ion separation instrument.

GB-2502650 (Micromass) discloses an adaptive and targeted control of ion populations to improve the effective dynamic range of a mass analyser.

US 2011/0183431 (Covey) discloses a mass analysis system with low pressure differential mobility spectrometer.

"Atmospheric pressure ion trapping in a tandem FAIMS-FAIMS coupled to a TOFMS: Studies with electrospray generated gramicidin S ions" (Guevremont et al.), J Am Soc Mass Spectrom. 2001 December; 12(12): 1320-30 discloses a tandem FAIMS-FAIMS system for ion trapping at room temperature and atmospheric pressure.

US 2012/119078 (Micromass) discloses an ion population control device for a mass spectrometer.

It is desired to provide an improved method of mass spectrometry.

SUMMARY

According to an aspect there is provided a method of mass spectrometry comprising:

separating a first population of ions according to their ion mobility;

selectively attenuating ions in the first population of ions in one or more ion mobility and/or drift time ranges so as to form a second population of ions, wherein the step of selectively attenuating ions comprises applying a varying, increasing or decreasing attenuation factor to ions in different ion mobility and/or drift time ranges; and separating the second population of ions according to their ion mobility.

Applying a varying, increasing or decreasing attenuation factor to ions in different ion mobility and/or drift time ranges means that it is possible to control the amount of attenuation applied to, for example, high mobility ions. This represents an improvement over conventional arrangements, such as the pre-concentrator of U.S. Pat. No. 7,105,808 (Bromberg), which cannot control the amount of ions that are transferred in different ion mobility and/or drift time ranges. No data dependent or targeted operation is disclosed. The purpose is only to remove high mobility species.

The disclosed embodiments are also distinct from the arrangements disclosed in US 2002/0014586 (Clemmer) and U.S. Pat. No. 6,498,342 (Clemmer) in that the arrangements which are disclosed apply a constant, rather than a varying, increasing or decreasing attenuation factor to ions in different ion mobility and/or drift time ranges.

Embodiments of the present disclosure also allow ions to be attenuated prior to performing an analytical ion mobility separation.

The ion mobility and/or drift time ranges may be attenuated such that the largest signal within the ion mobility spectrum does not exceed a fixed amplitude threshold, which ion mobility spectrum is optionally determined by a pre-scan.

To alleviate space charge issues in the ion mobility spectrometer or separator it may be desirable to attenuate the ion signal only within specific ion mobility and/or drift time ranges and so avoid changing the transmission of ions in the same population of ions which are not affected by space charge interaction distortion.

The method may further comprise accumulating the second population of ions in an accumulation device or region such that the second population of ions is not separated according to ion mobility and/or drift time prior to the step of separating the second population of ions according to their ion mobility.

This accumulation step may provide an improved resolution of ions and/or improved analysis of ions since ions from different drift time ranges (in the second population of ions) may be brought together before being separated again according to ion mobility.

The step of selectively attenuating ions may comprise selectively attenuating one or more relatively abundant or intense species of ions. The step of attenuating ions may comprise selectively attenuating only one or more relatively abundant or intense species of ions. Alternatively, the step of attenuating ions may comprise selectively attenuating all ions except one or more relatively abundant or intense species of ions.

The step of selectively attenuating ions may comprise:

(i) depleting one or more species of ions or completely removing one or more species of ions; and/or (ii) attenuating one or more species of ions by at least about 10%, about 20%, about 30%, about 40%, about 50%, about 60%, about 70%, about 80%, about 90%, about 95% or about 100%.

The step of selectively attenuating one or more relatively abundant or intense species of ions optionally comprises:

(i) resonantly ejecting one or more relatively abundant or intense species of ions from an ion trap; and/or (ii) resonantly ejecting one or more relatively abundant or intense species of ions from a continuous ion beam using a quadrupole rod set mass filter; and/or (iii) separating a population of ions by ion mobility separation and then attenuating one or more relatively abundant or intense species of ions by time dependent attenuation of ions having ion mobilities within one or more particular ion mobility ranges; and/or (iv) separating a population of ions by axial time of flight separation and then attenuating one or more relatively abundant or intense species of ions by time dependent attenuation; and/or (v) filtering a population of ions one or more times with one or more non-overlapping mass or mass to charge ratio ranges and/or one or more non-overlapping ion mobility ranges and then accumulating ions having mass or mass to charge ratios and/or ion mobilities within the one or more non-overlapping mass or mass to charge ratio ranges and/or the one or more non-overlapping ion mobility ranges within an ion trap; and/or (vi) passing a population of ions into a mass filter and scanning the mass filter over a mass or mass to charge ratio range at a speed or with a dwell time that is dependent on mass or mass to charge ratio; and/or (vii) attenuating one or more relatively abundant or intense species of ions using one or more devices operating in series; and/or (viii) stepping a mass filter or quadrupole mass filter and varying the dwell time as the mass filter or quadrupole mass filter is being stepped.

The step of separating the first population of ions may be carried out in a first upstream ion mobility spectrometer or separator and the step of separating the second population of ions may be carried out in a second downstream ion mobility spectrometer or separator. An accumulation device is optionally located or positioned between the first upstream ion mobility spectrometer or separator and the second downstream ion mobility spectrometer or separator.

The accumulation and separation times of the first and second ion mobility spectrometers or separators may be synchronised.

Either or both of the first and second ion mobility spectrometers or separators may be operated as a substantially mass separating device.

The method may further comprise changing or optimising one or more conditions or parameters of the second downstream ion mobility spectrometer or separator based on the composition of the second population of ions. The one or more conditions or parameters may comprise one or more of resolution, space charge capacity, drift gas composition, chemically selective dopants, travelling wave velocity, velocity ramp, travelling wave amplitude and amplitude ramp.

The method may further comprise operating the first upstream ion mobility spectrometer or separator under greater, lesser, the same or different parameters and/or conditions to the second downstream ion mobility spectrometer or separator. The operating parameters and/or conditions may comprise one or more of resolution, space charge capacity, drift gas composition, chemically selective dopants, travelling wave velocity, velocity ramp, travelling wave amplitude and amplitude ramp.

The first ion mobility spectrometer or separator may have a first elution time and/or cycle time and/or resolution and the second ion mobility spectrometer or separator may have a second elution time and/or cycle time and/or resolution, wherein optionally the first elution time and/or cycle time and/or resolution is lower or shorter than the second elution time and/or cycle time and/or resolution.

The elution, drift or transit time of one or more species, or a given species of ions through the first ion mobility spectrometer or separator and/or the second ion mobility spectrometer or separator may be in the range: (i) about 0-1 ms; (ii) about 1-2 ms; (iii) about 2-3 ms; (iv) about 3-4 ms; (v) about 4-5 ms; (vi) about 5-6 ms; (vii) about 6-7 ms; (viii) about 7-8 ms; (ix) about 8-9 ms; (x) about 9-10 ms; (xi) about 10-11 ms; (xii) about 11-12 ms; (xiii) about 12-13 ms; (xiv) about 13-14 ms; (xv) about 14-15 ms; (xvi) about 15-16 ms; (xvii) about 16-17 ms; (xviii) about 17-18 ms; (xix) about 18-19 ms; (xx) about 19-20 ms; (xxi) about 20-21 ms; (xxii) about 21-22 ms; (xxiii) about 22-23 ms; (xxiv) about 23-24 ms; (xxv) about 24-25 ms; (xxvi) about 25-26 ms; (xxvii) about 26-27 ms; (xxviii) about 27-28 ms; (xxix) about 28-29 ms; (xxx) about 29-30 ms; (xxxi) about 30-35 ms; (xxxii) about 35-40 ms; (xxxiii) about 40-45 ms; (xxxiv) about 45-50 ms; (xxxv) about 50-55 ms; (xxxvi) about 55-60 ms; (xxxvii) about 60-65 ms; (xxxviii) about 65-70 ms; (xxxix) about 70-75 ms; (xi) about 75-80 ms; (xli) about 80-85 ms; (xlii) about 85-90 ms; 90-95 ms; (xliv) about 95-100 ms; and (xlv) about >100 ms.

The cycle time of the first ion mobility spectrometer or separator may be less than the cycle time of the second ion mobility spectrometer or separator. Separations and attenuations of further populations of ions may be performed before separating the second and further attenuated populations of ions according to ion mobility in the second ion mobility spectrometer or separator.

The first ion mobility spectrometer or separator may have a relatively fast elution time of, for example, about 2 ms for a given ion species, and the second ion mobility spectrometer or separator may have a relatively slow elution time of, for example, about 20 ms for the same species. As such, ions can optionally accumulate in the accumulation device or region about 10 times for each cycle of the second ion mobility spectrometer or separator.

The second ion mobility spectrometer or separator may have an elution time that is at least double, triple or quadruple that of the first ion mobility spectrometer or separator.

The first ion mobility spectrometer or separator and/or the second ion mobility spectrometer or separator may comprise one or more DC field and/or travelling wave devices.

The first ion mobility spectrometer or separator and/or the second ion mobility spectrometer or separator may comprise a plurality of electrodes each having an aperture through which ions are transmitted in use. The method may further comprise supplying an RF voltage to the electrodes in order to radially confine ions within the first ion mobility spectrometer or separator and/or the second ion mobility spectrometer or separator.

The method may further comprise applying an attenuation factor of greater than or less than about 10%, about 20%, about 30%, about 40%, about 50%, about 60%, about 70%, about 80%, about 90% to ions in each of said one or more ion mobility and/or drift time ranges to form said second population of ions.

The method may further comprise applying an attenuation factor of between 10-90%, 20-80%, 30-70% or 40-60% to ions in each of said one or more ion mobility and/or drift time ranges to form said second population of ions.

The method may further comprise applying an attenuation factor of about 0% and/or about 100% to ions in each of said one or more ion mobility and/or drift time ranges to form said second population of ions.

The method may further comprise recording the amount of attenuation applied for each ion mobility and/or drift time range, and optionally calculating a correction factor to be applied to mass spectral data produced from the populations of ions, and optionally applying the correction factor to mass spectral data produced from the populations of ions.

The method may further comprise separating one or more further populations of ions according to ion mobility, and attenuating ions in the further populations of ions so as to form further attenuated populations of ions.

The step of selectively attenuating ions may comprise applying a varying, increasing or decreasing attenuation factor to ions in different populations of ions.

The method may further comprise accumulating and mixing the second and further attenuated populations of ions in the accumulation device and subsequently separating the second and further attenuated populations of ions simultaneously according to ion mobility.

The method may further comprise accumulating the second and further attenuated populations of ions in the accumulation device and subsequently separating the second and further attenuated populations of ions simultaneously according to ion mobility, wherein the second and further attenuated populations of ions are optionally kept separate from one another during said accumulation and/or separation thereof. The second and further populations of ions are optionally travelling through a or the second ion mobility spectrometer or separator at substantially the same time whilst being kept separate from one another.

The method may further comprise recording the amount of attenuation applied for each ion mobility and/or drift time range, and/or each different population of ions, and optionally calculating a correction factor to be applied to mass spectral data produced from the populations of ions, and optionally applying the correction factor to mass spectral data produced from the populations of ions.

The method may further comprise the step of detecting the second and/or further populations of ions, optionally using an ion detector.

The method may further comprise performing a pre-scan to determine an intensity profile and/or charge profile and/or mobility spectrum, optionally at a plurality of ion mobility and/or drift time regions.

The method may further comprise accumulating ions that have not been attenuated, and/or have not been completely attenuated and/or have been attenuated to a lesser degree, in the accumulation device optionally whilst said second population of ions are separated according to their ion mobility.

The method may further comprise fragmenting said second population of ions by Electron Transfer Dissociation prior to separating said second population of ions according to ion mobility, optionally within an or the accumulation device.

In embodiments, in the process of Electron Transfer Dissociation either:

(a) the parent or analyte ions are fragmented or are induced to dissociate and form the product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form the product or fragment ions; and/or (c) the parent or analyte ions are fragmented or are induced to dissociate and form the product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form the product or fragment ions; and/or (e) electrons are transferred from one or more neutral, non-ionic or uncharged superbase reagent gases or vapours to one or more multiply charged analyte cations or positively charged ions whereupon at least some of the multiply charged analyte cations or positively charged ions are induced to dissociate and form the product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form the product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form the product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The method may further comprise performing, optionally within an or the accumulation device, one or more processes on said second population of ions. The one or more processes may cause parent or precursor ions in the second population of ions to fragment and/or react to produce fragment or product ions. The fragment or product ions may then be separated according to their ion mobility. The step of separating the second population of ions according to their ion mobility may be replaced by or comprise separating the fragment or product ions according to their ion mobility. The one or more processes may comprise at least one of Electron Transfer Dissociation, Collision Induced Dissociation, charge stripping, supercharging, ion molecule interactions, and ion-ion interactions. The one or more processes may indirectly attenuate the second population of ions.

According to an aspect of the present disclosure there is provided a mass spectrometer comprising:

a first ion mobility spectrometer or separator arranged and adapted to separate a first population of ions according to their ion mobility;

an attenuation device arranged and adapted to apply a varying, increasing or decreasing attenuation factor to ions in different ion mobility and/or drift time ranges, so as to attenuate ions in the first population of ions in one or more ion mobility and/or drift time ranges and to form a second population of ions; and a second ion mobility spectrometer or separator arranged and adapted to subsequently separate the second population of ions according to their ion mobility.

The mass spectrometer may further comprise an accumulation device or region arranged and adapted to accumulate the second population of ions such that the second population of ions are not separated according to ion mobility and/or drift time.

The accumulation device or region may be located between the first and second ion mobility spectrometers or separators. The mass spectrometer may further comprise a further accumulation device or region upstream of the first ion mobility spectrometer or separator. The further accumulation device or region may be arranged and adapted to accumulate the first or further population(s) of ions, optionally prior to introducing the first or further population(s) of ions into the first ion mobility spectrometer or separator.

The mass spectrometer may further comprise a mass to charge ratio filter or separator, for example a Time of Flight mass analyser or quadrupole filter. The mass to charge ratio filter or separator may be positioned upstream of the first ion mobility spectrometer or separator and/or the further accumulation device.

The attenuation device is optionally synchronised to the release of ions from the first ion mobility spectrometer or separator.

The further ion accumulation device or region is optionally an RF ion accumulation device or region for radially confining ions therein, and is optionally followed by the first ion mobility spectrometer or separator which is optionally an RF ion mobility spectrometer or separator for radially confining ions therein. The attenuation device or region is optionally positioned downstream of the first ion mobility spectrometer or separator. The attenuation device or region may comprise a defocusing or deflecting lens.

The accumulation device or region and second ion mobility spectrometer or separator are optionally positioned downstream of the attenuation device.

In accordance with various embodiments, as ions pass from the first ion mobility spectrometer or separator to the accumulation device or region the ions are optionally attenuated by differing amounts at different ion mobilities and/or drift times. The second population of ions accumulated in the accumulation device or region is subsequently separated in the second ion mobility spectrometer or separator according to ion mobility.

According to various embodiments the first ion mobility spectrometer or separator and the attenuation device are optionally used to condition the first ion population. This arrangement optionally allows the ion concentration to be adjusted over particular ion mobility or drift time ranges such that the performance of the second ion mobility spectrometer or separator is optionally optimised. It is envisaged that the first ion mobility spectrometer or separator is optionally a lower performance ion mobility spectrometer or separator and/or optionally has a higher space charge tolerance than the second ion mobility spectrometer or separator. The first ion mobility spectrometer or separator may have a similar or faster separation time as the second ion mobility spectrometer or separator.

According to an aspect of the present disclosure there is provided a method of mass spectrometry comprising:

accumulating a first population of ions in a first upstream accumulation device;

separating a first population of ions in a first ion mobility spectrometer or device;

altering the transmission of at least some ions exiting the first ion mobility spectrometer or device using an attenuation device or lens depending of their mobility elution time to produce a second population of ions;

accumulating the second population of ions in a second accumulation region down-stream of the attenuation device or lens such that any ion mobility separation is lost;

separating said second population of ions in a second ion mobility spectrometer or device down-stream of the second accumulation region; and detecting said second, separated population of ions.

The accumulation and separation time of both ion mobility spectrometers or devices may be synchronized.

The first ion mobility spectrometer or device may have substantially lower ion mobility performance and greater space charge capacity than the second ion mobility spectrometer or device.

The ion mobility separation conditions of the second ion mobility spectrometer or device may be changed to be optimized for the mobility range accumulated in the second ion accumulation device for any given ion mobility separation cycle.

The ion mobility drift gas composition may be substantially different in the first ion mobility spectrometer or device and the second ion mobility spectrometer or device.

Either or both the first and second ion mobility spectrometer or device may be operated as a substantially mass separating device.

A mass or mass to charge ratio filter or separator, for example a Time of Flight analyser, may be positioned upstream or downstream of any of the devices.

The accumulation devices or regions, and the first or second ion mobility spectrometers or devices, may have radial RF confinement.

Ion mobility separation of the first population of ions may occur during the separation of a previously accumulated population of ions.

Whilst ions are separating in the first ion mobility spectrometer or separator, one or more further populations of ions may accumulate in the first accumulation device, and whilst ions are separating in the second ion mobility spectrometer or separator, one or more further populations of ions may be accumulated in the second accummulation device. The one or more further populations of ions may have not been attenuated, and/or have not been completely attenuated and/or have been attenuated to a lesser degree than said first population of ions. This may result in situations where ions are accumulating in both accumulation devices at the same time. Ions may pass through the attenuation device or lens with between about 10-90%, about 20-80%, about 30-70%, about 40-60%, about 50% transmission, or substantially about 100% transmission.

According to an aspect of the present disclosure there is provided a method of mass spectrometry comprising:

separating a first population of ions according to their ion mobility;

selectively attenuating ions in the first population of ions in one or a plurality of ion mobility and/or drift time ranges so as to form a second population of ions; and accumulating the second population of ions in an accumulation device or region such that the second population of ions is not separated according to ion mobility and/or drift time, and subsequently separating said second population of ions according to their ion mobility.

According to an aspect of the present disclosure there is provided a mass spectrometer comprising:

a first ion mobility spectrometer or separator arranged and adapted to separate a first population of ions according to their ion mobility;

an attenuation device arranged and adapted to attenuate ions in the first population of ions in one or more ion mobility and/or drift time ranges so as to form a second population of ions;

an accumulation device or region arranged and adapted to accumulate the second population of ions such that the second population of ions are not separated according to ion mobility and/or drift time; and a second ion mobility spectrometer or separator arranged and adapted to subsequently separate the second population of ions according to their ion mobility.

According to an aspect of the present disclosure there is provided a method of mass spectrometry comprising:

accumulating a first population of ions in a first accumulation device or region;

separating the first population of ions according to their ion mobility;

selectively attenuating ions in the first population of ions in one or more ion mobility and/or drift time ranges so as to form a second population of ions.

The step of selectively attenuating ions may comprise applying a varying, increasing or decreasing attenuation factor to ions in different ion mobility and/or drift time ranges.

The first accumulation device or region may comprise an ion trap. The method may further comprise providing an attenuation device for selectively attenuating ions. The attenuation device may comprise a deflection lens or defocusing lens. The method may further comprise providing a first ion mobility spectrometer or separator for separating the first population of ions according to their ion mobility. The first ion mobility spectrometer or separator is optionally downstream of the first accumulation device or region. The attenuation device is optionally downstream of the first ion mobility spectrometer or separator.

The method may further comprise accumulating the second population of ions in a second accumulation device or region, which is optionally downstream of the attenuation device. The second accumulation device or region may comprise an ion trap.

The method may further comprise separating the second population of ions according to their ion mobility in optionally a second ion mobility spectrometer or separator. The second ion mobility spectrometer or separator may be downstream of the second accumulation device or region.

The method may further comprise attenuating ions by differing amounts at different drift times as ions pass from the first ion mobility spectrometer or separator to the second accumulation device or region.

The cycle time of the first ion mobility spectrometer or separator may be less than the cycle time of the second ion mobility spectrometer or separator. Separations and attenuations of further populations of ions may be performed before separating the second and further attenuated populations of ions according to ion mobility in the second ion mobility spectrometer or separator.

The first ion mobility spectrometer or separator may have a relatively fast elution time of, for example, about 2 ms for a given ion species, and the second ion mobility spectrometer or separator may have a relatively slow elution time of, for example, about 20 ms for the same species. As such, ions can optionally accumulate in the second accumulation device or region about 10 times for each cycle of the second ion mobility spectrometer or separator.

According to an aspect of the present disclosure there is provided a mass spectrometer comprising:

a first accumulation device or region arranged and adapted to accumulate a first population of ions;

a first ion mobility spectrometer or separator arranged and adapted to separate the first population of ions according to their ion mobility; and an attenuation device arranged and adapted to selectively attenuate ions in the first population of ions in one or more ion mobility and/or drift time ranges so as to form a second population of ions.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

An embodiment will now be described.

Figure 1:
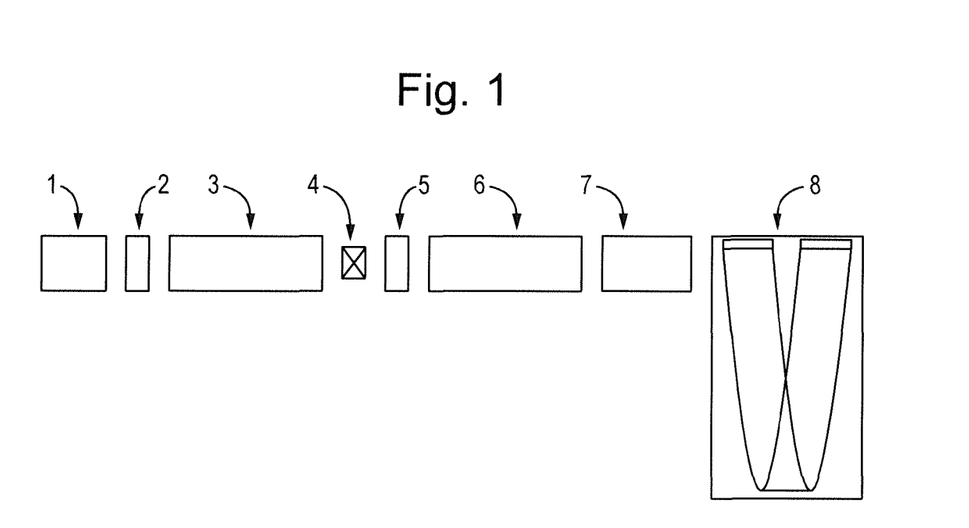
FIG. 1 shows a mass spectrometer according to an embodiment and comprises a first ion mobility spectrometer or separator provided upstream of a second ion mobility spectrometer or separator and wherein an attenuation device is provided downstream of the first ion mobility spectrometer or separator.

FIG. 1 shows an embodiment wherein ions are optionally produced in an ion source 1 and the ions are then optionally accumulated in a first ion accumulation device 2. A pulse of ions from the first ion accumulation device 2 is optionally passed into a first ion mobility spectrometer or separator 3. Ions are optionally separated according to their ion mobility in the first ion mobility spectrometer or separator 3.

Ions or an ion flux emerging from the first ion mobility spectrometer or separator 3 is optionally attenuated by an attenuation device 4. The amount or degree of attenuation or the attenuation factor is optionally set to differ depending on, for example, the elution time and/or ion mobility and/or drift time of the ions separated in the first ion mobility spectrometer or separator 3. The operation of the attenuation device 4 is optionally synchronised to or with the release of ions from the first ion accumulation device 2 and the ion mobility and/or drift time of ions separated in the first ion mobility spectrometer or separator 3.

The attenuation factor applied at each ion mobility and/or drift time for each release of ions from the first ion accumulation device 2 may be recorded to allow, for example, rescaling of final data detected by a detector. This allows quantitative information to be retained.

Attenuated and optionally non-attenuated ions exiting the attenuation device 4 is optionally accumulated in a second ion accumulation device 5 which is arranged downstream of the attenuation device 4. At this point any ion mobility separation provided by the first ion mobility spectrometer or separator 3 is essentially lost.

In some embodiments several populations of ions released from the first ion accumulation device 2 may be separated and/or attenuated and/or accumulated in the second ion accumulation device 5 optionally during an accumulation period. Ions may then be allowed to exit from the second ion accumulation device 5 after the accumulation period. When this accumulation period is over, the entire population of ions in the second ion accumulation device 5, optionally including any attenuated and non-attenuated ions, may then be released into a second ion mobility spectrometer or separator 6. Ions optionally exit the second ion mobility spectrometer or separator 6 according to their ion mobility and/or drift time, and the ions may pass though one or more downstream devices 7 such as fragmentation devices and analytical filters (e.g. quadrupole mass filters or other devices). Ions may then be detected directly or, as shown in FIG. 1, ions may according to various embodiments be directed to an orthogonal acceleration Time of Flight mass analyser 8.

The first ion mobility spectrometer or separator 3 and the second ion mobility spectrometer or separator 6 may comprise DC field devices or travelling wave devices, and each may be operated under the same parameters and/or conditions or different parameters and/or conditions of ion mobility separation. For example, different collision gases or chemically selective dopants may be present in the first ion mobility spectrometer or separator 3 and the second ion mobility spectrometer 6 or separators.

In an embodiment ions in one or more ion mobility and/or drift time ranges may be attenuated in a data dependent manner before optionally being separated by the second ion mobility spectrometer or separator 6 to optionally control saturation of the ion detector and/or detection electronics, and/or distortions in the ion mobility spectrometer or separator performance due to ion mobility specific, local space charge effects.

Figure 2:
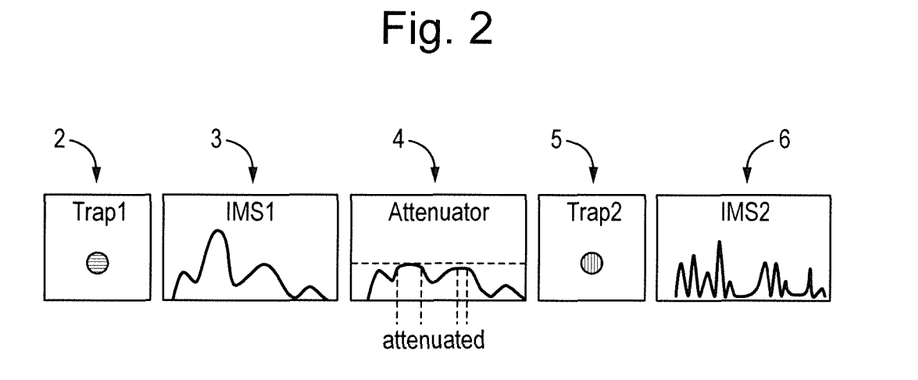
FIG. 2 shows a mass spectrometer according to an embodiment wherein a pre-scan is performed in the first ion mobility spectrometer or separator.

FIG. 2 further illustrates an embodiment.

A first ion accumulation device 2 is provided upstream of a first ion mobility spectrometer or separator 3. A short pre-scan is optionally carried out in the first ion mobility spectrometer or separator 3 and/or the second ion mobility spectrometer or separator 6 to optionally determine the charge in one or more ion mobility and/or drift time ranges. The ion mobility and/or drift time spectrum is depicted within the first ion mobility spectrometer or separator 3 in FIG. 2 and optionally represents the signal produced during a pre-scan in which ions are only separated in the first ion mobility spectrometer or separator 3.

Ions analysed during the pre-scan optionally pass through all other downstream devices before detection (or bypass one or more of these devices and/or are detected using a separate detection system, which is optionally not on the main ion path). The pre-scan may comprise a short scan performed before each longer analytical scan and/or information may be taken from a previous analytical scan. Many different data dependent methods are known and may be applied. However, according to various embodiments the pre-scan optionally determines not only the total charge in the ion population but also the distribution of that charge within the ion mobility separation.

The attenuation device 4, which may comprise an electrostatic lens, is optionally used to control the charge entering the second ion accumulation device 5 for one or more ion mobility and/or drift time ranges optionally eluting from the first ion mobility spectrometer or separator 3 in a subsequent analysis.

The ion mobility and/or drift time spectrum illustrated within the attenuation device 4 in FIG. 2 optionally represents the population of ions entering the second ion accumulation device 5 in the subsequent analysis. Attenuation of two ion mobility and/or drift time ranges is optionally shown with dotted lines in FIG. 2. These ranges have optionally been attenuated such that the largest signal within the ion mobility and/or drift time spectrum does not exceed a fixed amplitude threshold as depicted by the horizontal dotted line. A record may be made of the attenuation factor applied to each ion mobility and/or drift time range during operation of the system.

The entire population of ions after attenuation may be accumulated in the second ion accumulation device 5 and then optionally released into the second ion mobility spectrometer or separator 6. The second ion mobility spectrometer or separator 6 may have a higher resolution than the first ion mobility spectrometer or separator 3. The resultant mobilogram may contain ranges of data which have been attenuated such that space charge effects which could otherwise lead to shifts in drift time or peak broadening for specific ion mobility and/or drift time ranges are optionally minimized so that the detection system is optionally not saturated such very intense signals in these ranges.

A correction factor may be calculated for the one or more ion mobility and/or drift time ranges eluting from the second ion mobility spectrometer or separator 6 based on the time and magnitude of the attenuation factor(s) which are optionally applied.

A further embodiment will now be described.

Figure 3:
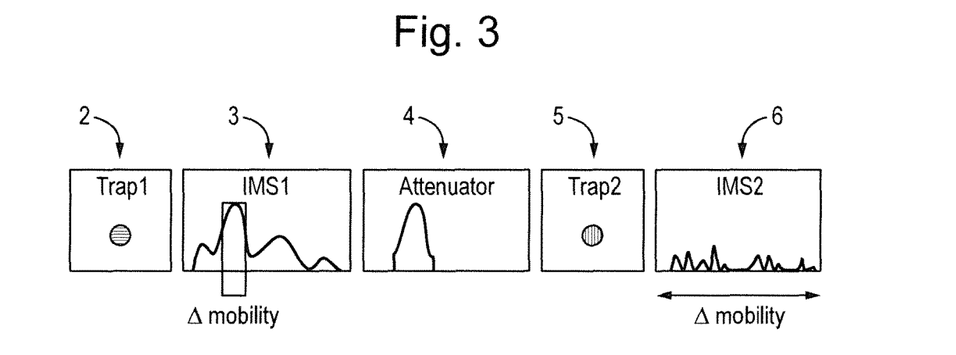
FIG. 3 shows a mass spectrometer according to another embodiment wherein ions having ion mobilities within a certain range are selected.

FIG. 3 illustrates a second embodiment. For targeted analysis the ion mobility and/or drift time range(s) of one or more target species is optionally known. It may be desirable to remove ions from other ion mobility and/or drift time ranges before optionally injecting ions into the second ion mobility spectrometer or separator 6. In this case one or more attenuation factors are optionally applied to the attenuation device 4 such that ions outside one or more ion mobility and/or drift time ranges are at least partially attenuated or attenuated to substantially zero transmission. Ions within the one or more ion mobility and/or drift time ranges are optionally accumulated in the second ion accumulation device 5 and are then optionally subsequently pulsed into the second ion mobility spectrometer or separator 6.

The one or more ion mobility and/or drift time ranges may be chosen to change with chromatographic retention time in a predetermined way optionally based on prior knowledge of chromatographic elution time.

Once the one or more ion mobility and/or drift time ranges have been chosen, the ion mobility separation conditions in the second ion mobility spectrometer or separator 6, such as travelling wave velocity and/or velocity ramp and/or wave amplitude and/or amplitude ramp, may be selected to optimize the separation of ions within the one or more ion mobility and/or drift time ranges as they pass through the second ion mobility spectrometer or separator 6.

According to the embodiment which is shown and described with reference to FIG. 3, the one or more ion mobility and/or drift time ranges are optionally shown as a rectangle in the ion mobility and/or drift time spectrum in the first ion mobility spectrometer or separator 3. The width of the rectangle optionally covers an ion mobility and/or drift time range, indicated by Δmobility. The attenuated signal is shown in the attenuation device 4. The ion mobility and/or drift time spectrum shown in the second ion mobility spectrometer or separator 6 optionally indicates that the conditions in the second ion mobility spectrometer or separator 6 have been adjusted, such that the ion mobility and/or drift time range, Δmobility, optionally elutes over a time period adapted to the known range of ion mobilities and/or drift times delivered by the second ion accumulation device 5.

For example, in a screening experiment the one or more ion mobility and/or drift time ranges over which the targets elute is known. This range or ranges may be selected, then optionally introduced into the second ion accumulation device 5 and may then be pulsed into the second ion mobility spectrometer or separator 6. The second ion mobility spectrometer or separator 6 may be optimized for the one or more ion mobility and/or drift time ranges.

This embodiment optionally ensures that few or substantially no ions of relatively low ion mobility and/or drift time remain in the second ion mobility spectrometer or separator 6 when a subsequent population of ions is optionally pulsed into the second ion mobility spectrometer or separator 6. This optionally negates any requirement to wait for ions of relatively low ion mobility and/or drift time to leave the second ion mobility spectrometer or separator 6 between cycles. Both space charge tolerance and acquisition system dynamic range are optionally improved.

One or more ion mobility and/or drift time ranges may be selected, and the separation period, or elution time, of the first ion mobility spectrometer or separator 3 may be short compared to the separation period, or elution time, of the second ion mobility spectrometer or separator 6. In this case multiple packets of ions may be pulsed into the first ion mobility spectrometer or separator 3 and optionally accumulated in the second ion accumulation device 5. The accumulated packets of ions may then be pulsed into the second ion mobility spectrometer or separator 6 simultaneously or separately.

Generally, ions that have not been attenuated may be accumulated in the second accumulation device 5 during the ion mobility separation of ions in the second ion mobility spectrometer or separator 6. This optionally results in 100% duty cycle for those ions which are transmitted without attenuation.

A further embodiment will now be described.

Figure 4:
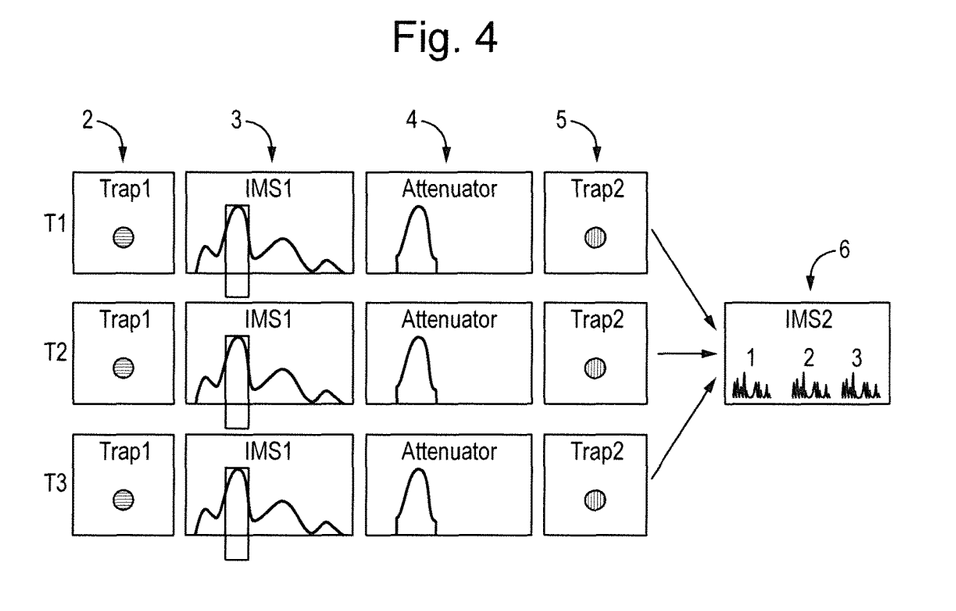
FIG. 4 shows a mass spectrometer according to another embodiment wherein the mass spectrometer is operated in a multiplexed mode of operation.

FIG. 4 shows a third embodiment optionally relating to multiplexed ion mobility spectrometer or separator operation. At time T1 a first population of ions may elute from the first ion mobility spectrometer or separator 3, and may be attenuated such that first ions within one or more first ion mobility and/or drift time ranges are optionally selected by the attenuation device 4. The first ions are then optionally accumulated in the second ion accumulation device 5. The first ions are then optionally pulsed into the second ion mobility spectrometer or separator 6 as a first pulse of ions.

As the first pulse of ions is travelling though the second ion mobility spectrometer or separator 6, the above process may be carried out for a second population of ions at a time T2, which is optionally later than the time T1. That is, at time T2 a second population of ions may elute from the first ion mobility spectrometer or separator 3, and may be attenuated such that second ions within one or more second ion mobility and/or drift time ranges are optionally selected by the attenuation device 4, which second ions may then be accumulated in the second ion accumulation device 5. The second ions may then be pulsed into the second ion mobility spectrometer or separator 6 as a second pulse of ions.

As the first and/or second pulses of ions are travelling though the second ion mobility spectrometer or separator 6, the above process may be carried out for a third population of ions at a time T3, which is optionally later than the time T1 and/or T2. That is, at time T3 a third population of ions may elute from the first ion mobility spectrometer or separator 3, and may be attenuated such that third ions within one or more third ion mobility and/or drift time ranges are optionally selected by the attenuation device 4, which third ions may then be accumulated in the second ion accumulation device 5. The third ions may then be pulsed into the second ion mobility spectrometer or separator 6 as a third pulse of ions.

It will be appreciated that the above process may continue for fourth and optionally further populations of ions.

As the one or more first and/or second and/or third and/or fourth and/or further ion mobility and/or drift time ranges are known the times at which ions are pulsed into the second ion mobility spectrometer or separator 6 may be arranged such that no overlapping or overtaking of ions occurs during separation of multiple ion populations.

In other words, the first and/or second and/or third and/or fourth and/or further populations and/or pulses of ions are optionally kept separate from one another as they travel through the second ion mobility spectrometer or separator 6 and/or mass spectrometer.

This simplifies the interpretation of the multiplexed data compared to multiplexed ion mobility data in which ion mobility ranges are not controlled or known. Furthermore, multiplexing in this manner optionally limits both detector system saturation and space charge effects.

The buffer gas composition may be different in the first ion mobility spectrometer or separator 3 and the second ion mobility spectrometer or separator 6. Different polarisable or polar dopants may be present in the first ion mobility spectrometer or separator 3 and the second ion mobility spectrometer or separator 6, so that optionally two dimensional ion mobility separations may be performed.

According to any of the embodiments described above, more than two ion mobility spectrometers or separators and/or accumulation devices and/or attenuation devices may be used to gain more selectivity.

Various embodiments may allow precise control of the population of ions introduced into a high performance ion mobility separator within specific mobility ranges. This allows the problems of detector saturation and space charge effects due to high ion flux within particular mobility ranges to be mitigated.

In addition, for targeted analysis, various embodiments may allow ion mobility separation conditions to be optimized for the specific drift time range of the target ions by attenuating ions outside the target ranges.

It is possible to control the attenuation value of specific mobility regions using various embodiments. This is in contrast to conventional arrangements in which all ions above a certain mobility are prevented from being transmitted.

The disclosure also allows a 100% duty cycle for ions of interest to be realised as ions are accumulated in RF confined trapping regions during the ion mobility separation of a previously accumulated population of ions, and not lost radially as in conventional arrangements.

Although the present disclosure has been described with reference to various embodiments, it will be understood by those skilled in the art that various changes in form and detail may be made without departing from the scope of the disclosure as set forth in the accompanying claims.

The invention claimed is:

1. A method of mass spectrometry comprising:
   accumulating a first population of ions in a first accumulation device;
   separating the first population of ions according to their ion mobility;

selectively attenuating ions in said first population of ions in one or more ion mobility and/or drift time ranges so as to form a second population of ions, wherein said step of selectively attenuating ions comprises applying a varying, increasing or decreasing attenuation factor to ions in different ion mobility and/or drift time ranges, wherein the attenuation factor applied to ions in each of said ion mobility and/or drift time ranges is less than about 90%;

accumulating said second population of ions in a second accumulation device or region; and separating said second population of ions according to their ion mobility, wherein:

said step of separating said first population of ions is carried out in a first ion mobility separator which is downstream of said first accumulation device;

said step of selectively attenuating ions in said first population of ions is carried out using an attenuation device, wherein the attenuation device is separate to and downstream of said first ion mobility separator;

said second accumulation device or region is downstream of said attenuation device; and said step of separating said second population of ions is carried out in a second ion mobility separator, wherein said second ion mobility separator is separate to and downstream of said attenuation device and said second accumulation device or region;

wherein said first ion mobility separator is a lower performance device having a first elution, cycle time or resolution and a first space charge tolerance and said second ion mobility separator is a higher performance device having a second elution, cycle time or resolution and a second space charge tolerance, wherein:

said first resolution is lower than said second resolution and said first space charge tolerance is greater than said second space charge tolerance; or said first elution or cycle time is shorter or faster than said second elution or cycle time and said first space charge tolerance is greater than said second space charge tolerance.

2. A method as claimed in claim 1, further comprising accumulating said second population of ions in the second accumulation device or region such that said second population of ions is not separated according to ion mobility and/or drift time within the second accumulation device or region and any ion mobility separation from the first ion mobility separator is lost, prior to said step of separating said second population of ions according to their ion mobility.

3. A method as claimed in claim 1, wherein said step of attenuating ions comprises selectively attenuating only one or more relatively abundant or intense species of ions.

4. A method as claimed in claim 1, wherein said step of attenuating ions comprises selectively attenuating all ions except one or more relatively abundant or intense species of ions.

5. A method as claimed in claim 1, further comprising determining one or more ion mobility and/or drift time ranges of said second population of ions that have been accumulated within the second accumulation device or region, and optimising one or more parameters of said second downstream ion mobility separator that will be applied to said second downstream ion mobility separator for said second population of ions based on the determined one or more ion mobility and/or drift time ranges of said second population of ions.

6. A method as claimed in claim 1, further comprising operating said first upstream ion mobility separator under different operating parameters or conditions to said second downstream ion mobility separator.

7. A method as claimed in claim 1, wherein said first ion mobility separator is a lower performance device having a first elution, cycle time or resolution and a first space charge tolerance and said second ion mobility separator is a higher performance device having a second elution, cycle time or resolution and a second space charge tolerance, wherein said first elution, cycle time or resolution is lower than said second elution, cycle time or resolution and said first space charge tolerance is greater than said second space charge tolerance.

8. A method as claimed in claim 1, wherein said first ion mobility separator comprises a plurality of electrodes each having an aperture through which ions are transmitted in use.

9. A method as claimed in claim 8, further comprising supplying an RF voltage to said electrodes to radially confine ions within said first ion mobility separator.

10. A method as claimed in claim 1, further comprising applying an attenuation factor of between 10-90%, 20-80%, 30-70% or 40-60% to ions in each of said one or more ion mobility and/or drift time ranges to form said second population of ions.

11. A method as claimed in claim 1, further comprising recording the amount of attenuation applied for each ion mobility and/or drift time range.

12. A method as claimed in claim 1, further comprising:

separating one or more further populations of ions according to ion mobility in said first ion mobility separator; and attenuating ions in said further populations of ions using said attenuation device so as to form further attenuated populations of ions, wherein the one or more further populations of ions have a composition substantially the same as that of the first population of ions, and an attenuation factor applied by said attenuation device to ions in said further populations of ions in each of said ion mobility and/or drift time ranges is substantially the same as the attenuation factor applied by said attenuation device to ions in said second population of ions in each of said ion mobility and/or drift time ranges.

13. A method as claimed in claim 12, wherein said step of selectively attenuating ions comprises applying a varying, increasing or decreasing attenuation factor to ions in different populations of ions.

14. A method as claimed in claim 1, further comprising recording the amount of attenuation applied for each different population of ions or each ion mobility and/or drift time range, and calculating a correction factor to be applied to each ion mobility and/or drift time range in mass spectral data produced from said populations of ions.

15. A method as claimed in claim 12, further comprising accumulating and mixing said second and further attenuated populations of ions in the second accumulation device or region and subsequently separating said second and further attenuated populations of ions in said second ion mobility separator simultaneously according to ion mobility.

16. A method as claimed in claim 12, further comprising accumulating and mixing said second and further populations of ions in the second accumulation device or region, wherein said second and further populations of ions are held within the second accumulation device such that said second and further populations of ions are not separated according to ion mobility and/or drift time within the second accumulation device or region and any ion mobility separation from the first ion mobility separator is lost and subsequently separating said second and further attenuated populations of ions simultaneously according to their ion mobility.

17. A method as claimed in claim 1, further comprising accumulating one or more further populations of ions that have not been attenuated, have not been completely attenuated, or have been attenuated to a lesser degree, in an accumulation device whilst said second population of ions are separated according to their ion mobility.

18. A method as claimed in claim 1, further comprising fragmenting or reacting said second population of ions prior to separating said second population of ions according to their ion mobility.

19. A mass spectrometer comprising:
- a first accumulation device or region arranged and adapted to accumulate a first population of ions;
- a first ion mobility separator downstream of said first accumulation device and arranged and adapted to separate the first population of ions according to their ion mobility;
- an attenuation device separate to and downstream of said first ion mobility separator, the attenuation device being arranged and adapted to apply a varying, increasing or decreasing attenuation factor to ions in different ion mobility and/or drift time ranges, so as to attenuate ions in said first population of ions in one or more ion mobility and/or drift time ranges and to form a second population of ions, wherein the attenuation factor applied to ions in each of said ion mobility and/or drift time ranges is less than about 90%;
- a second accumulation device or region downstream of said attenuation device; and
- a second ion mobility separator separate to and downstream of said second accumulation device or region, the second ion mobility separator being arranged and adapted to subsequently separate said second population of ions according to their ion mobility;

wherein said first ion mobility separator is a lower performance device having a first elution, cycle time or resolution and a first space charge tolerance and said second ion mobility separator is a higher performance device having a second elution, cycle time or resolution and a second space charge tolerance, wherein:

said first resolution is lower than said second resolution and said first space charge tolerance is greater than said second space charge tolerance; or said first elution or cycle time is shorter or faster than said second elution or cycle time and said first space charge tolerance is greater than said second space charge tolerance.

* * * * *